(12) United States Patent
Klotz

(10) Patent No.: US 9,913,720 B2
(45) Date of Patent: Mar. 13, 2018

(54) JOINT PROSTHESIS SYSTEM WITH POSITIONABLE HEAD

(71) Applicant: DePuy Synthes Products, LLC, Raynham, MA (US)

(72) Inventor: Conrad Klotz, Nappanee, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 732 days.

(21) Appl. No.: 14/162,452

(22) Filed: Jan. 23, 2014

(65) Prior Publication Data

US 2014/0135943 A1 May 15, 2014

Related U.S. Application Data

(62) Division of application No. 11/241,387, filed on Sep. 30, 2005, now Pat. No. 8,679,185.

(51) Int. Cl.
*A61F 2/30* (2006.01)
*A61F 2/40* (2006.01)

(52) U.S. Cl.
CPC ........ *A61F 2/30734* (2013.01); *A61F 2/4014* (2013.01); *A61F 2/40* (2013.01);
(Continued)

(58) Field of Classification Search
CPC .... A61F 2220/0033; A61F 2002/30332; A61F 2002/3625
See application file for complete search history.

(56) References Cited

U.S. PATENT DOCUMENTS 4,003,095 A   1/1977   Gristina
4,676,797 A   6/1987   Anapliotis et al.
(Continued)

FOREIGN PATENT DOCUMENTS

DE   4445892        6/1996
DE   19509037 C1    9/1996
(Continued)

OTHER PUBLICATIONS

Australian Search Report in Australian application AU2005247033, dated Apr. 23, 2010 (2 pages).
(Continued)

*Primary Examiner* — David Isabella
*Assistant Examiner* — Christine Nelson
(74) *Attorney, Agent, or Firm* — Maginot, Moore & Beck, LLP

(57) ABSTRACT

A method includes inserting a stem into a bone, positioning a solid articulating portion of a mounting element within a tapered bore so that the mounting element is substantially free to pivot in multiple degrees of freedom relative to the stem while maintaining substantially contiguous engagement between the solid articulating portion and a portion of a surface of the tapered bore defining a circle, engaging the joint component to the mounting element, manipulating the mounting element to vary an angular position of the joint component with the mounting element positioned in the tapered bore while maintaining the substantially contiguous engagement, and mechanically locking the solid articulating portion in the tapered bore to fix a position of the mounting element relative to the stem after manipulating the mounting element by forcing the solid articulating portion toward a bottom of the tapered bore.

13 Claims, 3 Drawing Sheets

(52) U.S. Cl.
CPC ... *A61F 2/4059* (2013.01); *A61F 2002/30329* (2013.01); *A61F 2002/30332* (2013.01); *A61F 2002/30378* (2013.01); *A61F 2002/30538* (2013.01); *A61F 2002/30542* (2013.01); *A61F 2002/30604* (2013.01); *A61F 2002/30772* (2013.01); *A61F 2002/30884* (2013.01); *A61F 2002/404* (2013.01); *A61F 2002/4018* (2013.01); *A61F 2002/4029* (2013.01); *A61F 2002/4044* (2013.01); *A61F 2002/4062* (2013.01); *A61F 2220/0025* (2013.01); *A61F 2220/0033* (2013.01); *A61F 2250/0006* (2013.01)

(56) References Cited

U.S. PATENT DOCUMENTS

| | | | |
|---|---|---|---|
| 4,822,370 | A | 4/1989 | Schelhas |
| 5,076,541 | A | 12/1991 | Daghe et al. |
| 5,080,685 | A | 1/1992 | Bolesky et al. |
| 5,314,479 | A | 5/1994 | Rockwood, Jr. et al. |
| 5,358,526 | A | 10/1994 | Tornier |
| 5,370,706 | A | 12/1994 | Bolesky et al. |
| 5,702,457 | A | 12/1997 | Walch et al. |
| 5,725,597 | A | 3/1998 | Hwang et al. |
| 5,741,335 | A | 4/1998 | Gerber et al. |
| 5,743,898 | A | 4/1998 | Bailey et al. |
| 5,910,143 | A | 6/1999 | Cripe et al. |
| 6,083,263 | A | 7/2000 | Draenert et al. |
| 6,197,062 | B1 | 3/2001 | Fenlin |
| 6,203,575 | B1 | 3/2001 | Farey |
| 6,206,925 | B1 | 3/2001 | Tornier |
| 6,228,120 | B1 | 5/2001 | Leonard et al. |
| 6,283,999 | B1 | 9/2001 | Rockwood, Jr. |
| 6,328,748 | B1 | 12/2001 | Hennig |
| 6,361,566 | B1 | 3/2002 | Al-Hafez |
| 6,408,931 | B1 * | 6/2002 | Tilak .................. B22D 11/049 164/459 |
| 6,478,500 | B1 | 11/2002 | Farenholtz |
| 6,558,425 | B2 | 5/2003 | Rockwood, Jr. |
| 6,620,197 | B2 | 9/2003 | Maroney et al. |
| 6,626,946 | B1 | 9/2003 | Walch et al. |
| 6,673,114 | B2 | 1/2004 | Hartdegen et al. |
| 6,736,851 | B2 | 5/2004 | Maroney et al. |
| 6,736,852 | B2 | 5/2004 | Callaway et al. |
| 6,749,637 | B1 | 6/2004 | Bahler |
| 6,776,799 | B2 | 8/2004 | Ball et al. |
| 6,863,690 | B2 | 3/2005 | Ball et al. |
| 6,953,478 | B2 | 10/2005 | Bouttens et al. |
| 7,192,449 | B1 | 3/2007 | McQueen et al. |
| 7,238,207 | B2 | 7/2007 | Blatter et al. |
| 7,431,736 | B2 | 10/2008 | Maroney et al. |
| 2001/0041940 | A1 | 11/2001 | Pearl |
| 2001/0053935 | A1 | 12/2001 | Hartdegen et al. |
| 2002/0016634 | A1 | 2/2002 | Maroney et al. |
| 2003/0014112 | A1 | 1/2003 | Ralph et al. |
| 2003/0040802 | A1 | 2/2003 | Errico et al. |
| 2003/0097183 | A1 | 5/2003 | Rauscher et al. |
| 2004/0002765 | A1 | 1/2004 | Maroney et al. |
| 2004/0010261 | A1 | 1/2004 | Hoag et al. |
| 2004/0030400 | A1 | 2/2004 | Horber |
| 2004/0064142 | A1 | 4/2004 | Ball et al. |
| 2004/0064188 | A1 | 4/2004 | Ball et al. |
| 2004/0064189 | A1 | 4/2004 | Maroney et al. |
| 2004/0122440 | A1 | 6/2004 | Daniels et al. |
| 2004/0167629 | A1 | 8/2004 | Geremakis et al. |
| 2005/0113931 | A1 | 5/2005 | Horber |
| 2005/0143829 | A1 * | 6/2005 | Ondrla .................. A61F 2/4014 623/19.14 |
| 2005/0149050 | A1 | 7/2005 | Stifter et al. |
| 2005/0187637 | A1 | 8/2005 | Karrer et al. |
| 2005/0251263 | A1 | 11/2005 | Forrer et al. |
| 2005/0288681 | A1 | 12/2005 | Klortz et al. |
| 2006/0142872 | A1 | 6/2006 | Klotz et al. |
| 2007/0078519 | A1 | 4/2007 | Klotz |
| 2007/0112430 | A1 | 5/2007 | Simmen et al. |
| 2012/0323250 | A1 | 12/2012 | Klotz et al. |
| 2014/0039508 | A1 | 2/2014 | Klotz et al. |

FOREIGN PATENT DOCUMENTS

| | | |
|---|---|---|
| DE | 19951141 | 5/2001 |
| DE | 10123517 | 11/2002 |
| DE | 202005020876 U1 | 10/2006 |
| EP | 0549480 A1 | 6/1993 |
| EP | 0679375 A1 | 11/1995 |
| EP | 0712617 A1 | 5/1996 |
| EP | 0715836 A1 | 6/1996 |
| EP | 0931522 A1 | 7/1999 |
| EP | 1314407 A1 | 5/2003 |
| EP | 1321114 A1 | 6/2003 |
| EP | 1393697 A1 | 3/2004 |
| EP | 1402856 A1 | 3/2004 |
| FR | 2731612 | 9/1996 |
| JP | 2004512922 | 5/2003 |
| WO | 9303688 A1 | 3/1993 |
| WO | 200122905 | 4/2001 |
| WO | 200239932 | 5/2002 |
| WO | 2003096939 | 11/2003 |

OTHER PUBLICATIONS

Australian Search Report in Australian application AU2005246996, dated Apr. 27, 2010 (3 pages).

Australian Search Report in Australian application AU2006225167, dated Mar. 22, 2011 (2 pages).

European Search Report in European application EP05257963.8, dated Dec. 20, 2007 (5 pages).

European Search Report in European application EP05257964.6, dated Dec. 20, 2007 (8 pages).

European Search Report in European application EP06255073.6, dated Jan. 5, 2007 (8 pages).

European Search Report in European application EP09162325.6, dated Oct. 2, 2009 (6 pages).

European Search Report in European application EP10178881.8, dated Mar. 10, 2011 (5 pages).

European Search Report in European application EP10178895.8, dated Dec. 14, 2010 (7 pages).

Japanese Office Action in Japanese application JP2005-378997, dated Feb. 9, 2010 (12 pages including translation).

The Mcelroy Translation Company, English translation of German Patent No. DE 101 23 517 Cl, dated Jan. 2006 (20 pages).

Japan Patent Office, Notification of Reasons for Refusal (Translation) associated with patent application 2006-267228, dated Oct. 5, 2010 (4 pages).

Japan Patent Office, Notification of Reasons for Refusal (Translation) associated with patent application 2009-138953, dated May 7, 2013 (4 pages).

* cited by examiner

JOINT PROSTHESIS SYSTEM WITH POSITIONABLE HEAD

This application is a divisional of U.S. application Ser. No. 11/241,387 filed Sep. 30, 2005 (now U.S. Pat. No. 8,679,185 issued Mar. 25, 2014), the entire contents of which is herein incorporated by reference.

This application is related to U.S. patent application Ser. No. 14/046,557, entitled "Joint Prosthesis System with Positionable Head", which was filed on Oct. 4, 2013 (now U.S. Pat. No. 9,681,954 issued Jun. 20, 2017), U.S. patent application Ser. No. 10/748,448, entitled "Joint Prosthesis with Infinitely Positionable Head", which was filed on Dec. 30, 2003 (now U.S. Pat. No. 8,419,798 issued Apr. 16, 2013); U.S. patent application Ser. No. 10/879,261, entitled "Instrumentation for Recording and Replicating Orthopaedic Implant Orientation", which was filed on Jun. 29, 2004 (now U.S. Pat. No. 8,273,093 issued Sep. 25, 2012); U.S. patent application Ser. No. 11/025,223, entitled "System and Method for Replicating Orthopaedic Implant Orientation", which was filed on Dec. 29, 2004 (now U.S. Pat. No. 8,460,390 issued Jun. 11, 2013); U.S. patent application Ser. No. 11/025,185, entitled "Joint Prosthesis with Infinitely Positionable Head", which was filed on Dec. 29, 2004 (now U.S. Pat. No. 8,444,698 issued May 21, 2013); and U.S. patent application Ser. No. 12/137,378, entitled "Joint Prosthesis with Positionable Head", which was filed on Jun. 11, 2008 (now U.S. Pat. No. 8,002,838 issued Aug. 23, 2011).

BACKGROUND AND SUMMARY

The present disclosure relates to joint prostheses, and particularly to prostheses having articulating head components. More specifically, the disclosure relates to a system for achieving variable positions for the head component of a joint prosthesis relative to a bone-engaging portion of the prosthesis.

Repair and replacement of human joints, such as the knee, shoulder, elbow and hip, has become a more and more frequent medical treatment. Longer life spans mean that the joints endure more wear and tear. More sports activities mean greater likelihood of serious joint injuries. Treatment of injuries, wear and disease in human joints has progressed from the use of orthotics to mask the problem, to fusion of the joint, to the use of prostheses to replace the damaged joint component(s).

As the success rate for total or partial joint replacements has increased, so too has the need for modularity and universality in the joint prosthesis. Patient variety means that no single size or configuration of joint prosthesis will suffice. The physical dimensions of a patient's joint components vary, as well as the bio-mechanic relationship between these components. For instance, in a shoulder prosthesis, the relationship between the articulating humeral and glenoid components can be significantly different between patients. These relationships are especially important where only one component of the joint is being replaced and must integrate with the existing natural opposing joint component.

For instance, in many shoulder surgeries, only the humeral component is replaced, leaving the glenoid component intact. In this case, it is imperative that the articulating surface of the humeral component match the articulating surface of the glenoid component as perfectly as possible, both statically and dynamically. With a typical humeral prosthesis, version and inclination are adjusted by the geometry of the head of the prosthesis. In other words, certain pre-determined head geometries are available that can be selected for a mating glenoid component. Absent an infinite variety of pre-determined head geometries, the resulting humeral prosthesis can often only achieve a best-fit relationship to the glenoid component of the shoulder joint.

In a typical surgical procedure, a trial component will be used to determine the optimum final component to be fixed to the bone. In most cases, the surgeon is able to make a good selection that fits the joint very well. However, in some cases, the accuracy of the fit cannot be determined until the surgery is completed and the patient has had an opportunity to exercise the repaired joint. Where significant problems arise, a revision surgery may be necessary to replace an improperly sized or configured joint component. One typical revision surgery requires removal of the entire prosthesis from the bone and replacement with a different prosthesis.

There is a significant need for a joint prosthesis that is both modular and universal. Such a prosthesis would be easily manipulated during the surgery and capable of achieving nearly infinite version and inclination angles. Moreover, an optimum prosthesis would be readily available for modification in a revision surgery without having to remove the entire prosthesis.

With the disclosed joint prosthesis a joint component is mounted to a bone engaging component of the prosthesis by an articulating mounting element. The articulating mounting element allows the joint component to adopt substantially infinitely variable ranges of angles in three dimensions relative to the bone engaging component.

In a one embodiment, the prosthesis is a humeral prosthesis for a shoulder replacement procedure. The humeral prosthesis includes a stem configured for engagement within the humerus. The stem defines a tapered bore facing the glenoid component of the shoulder joint. A distal portion of the mounting element is configured to be initially mobile within the bore, while a proximal end is configured to carry the humeral joint component or trial. The mounting element can be articulated to find the optimum position for the humeral joint component. The mounting element can then be temporarily tightened to hold the humeral joint component in position to verify the version and inclination angles of the component. The mounting element can be finally tightened to complete the humeral prosthesis.

The mounting element can be fixed in an orientation relative to the stem so as to fix the joint component in an orientation relative to the stem. Further, the mounting element and stem are configured to facilitate tightening the mounting element to the stem through achieving a friction fit with a tapered bore formed in the stem.

Several embodiments additionally utilize a second fixation mechanism. This second fixation mechanism includes a screw that is threaded into a threaded bore portion of the tapered bore in the stem. The screw bears against the mounting element to lock the element in position within the tapered bore.

The proximal portion of the mounting element defines a tapered surface that mates with a tapered feature of a head component for the humeral prosthesis. The head component can include an opening to access the passageway in the proximal portion of the mounting element, thereby providing access to the fixation screw in embodiments utilizing a fixation screw.

A number of joint components can be provided for interchangeable use to construct the prosthesis. For instance, a fixed mounting element can replace the articulating mounting element. Similarly, the head component for the joint prosthesis can be configured to mate directly with the stem, with the fixed mounting element or the articulating mounting element. The head component can also be modified to close the end of the passageway in the proximal portion of the articulating mounting element.

The joint prosthesis is advantageously both modular and adjustable. The joint prosthesis includes features that permit substantially infinitely variable positioning of a mating joint component relative to a bone engaging portion of the prosthesis.

The joint prosthesis is readily available for modification, whether during initial implantation or during a subsequent revision procedure. Preferably these features are combined in a joint prosthesis without creating a profile or prominence greater than is achieved by current joint prostheses.

In one embodiment, a method for mounting a joint component to a bone includes inserting a stem into the bone, positioning a solid articulating portion of a mounting element within a tapered bore associated with the stem so that the mounting element is substantially free to pivot in multiple degrees of freedom relative to the stem while maintaining substantially contiguous engagement between the solid articulating portion and a portion of a surface of the tapered bore defining a circle, engaging the joint component to a proximal portion of the mounting element, manipulating the mounting element to vary an angular position of the joint component relative to the stem with the mounting element positioned in the tapered bore while maintaining substantially contiguous engagement between the solid articulating portion and the portion of the surface of the tapered bore defining the circle, and mechanically locking the solid articulating portion in the tapered bore to fix a position of the mounting element relative to the stem after manipulating the mounting element by forcing the solid articulating portion toward a bottom of the tapered bore.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

The illustrative devices will be described hereinafter with reference to the attached drawings which are given as non-limiting examples only, in which.

Corresponding reference characters indicate corresponding parts throughout the several views.

DETAILED DESCRIPTION

Figure 1:
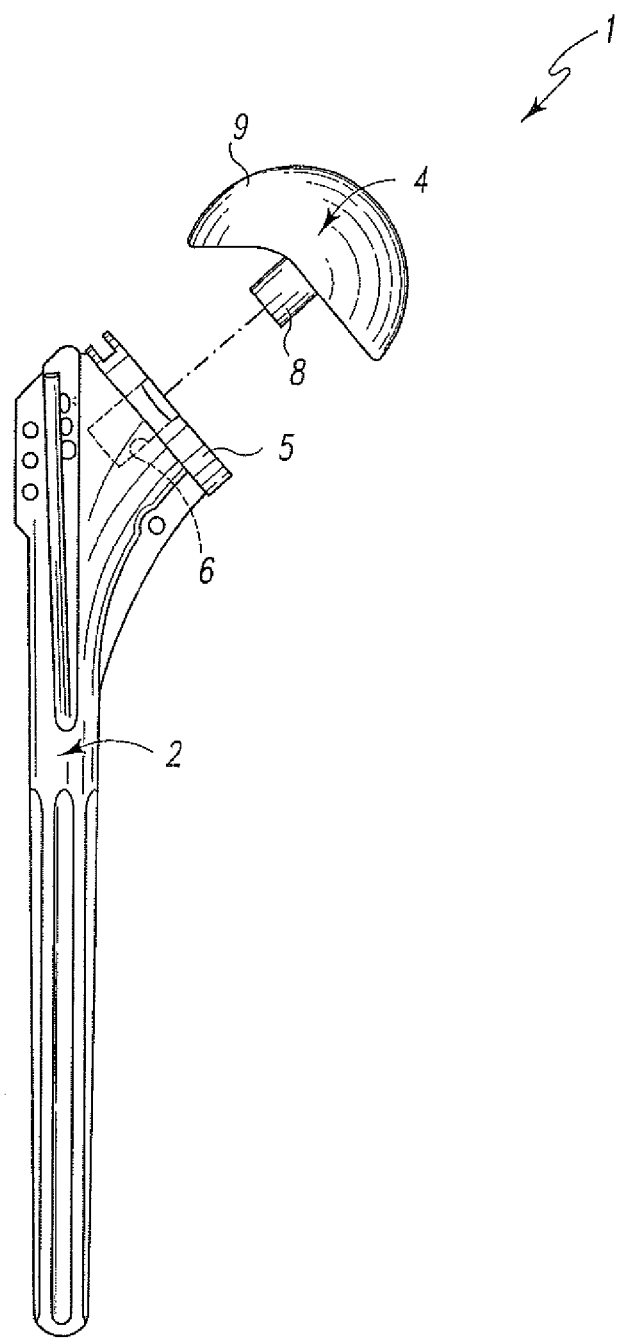
FIG. 1 is a side plan view of a typical prior art humeral prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

FIG. 1 is a side plan view of a typical prior art humeral prosthesis 1. The prosthesis 1 is the humeral component of a shoulder prosthesis that can be implanted in the humerus bone for articulating engagement with the natural glenoid or with a glenoid prosthesis. The prosthesis 1 includes a stem 2 configured to be implanted within the humerus bone in a conventional manner. The stem 2 forms a platform surface 5 that faces the glenoid component of the joint when the prosthesis is in its operative position. The platform surface 5 defines a tapered bore for use in mounting an articulating head component 4. The head component 4 includes a substantially uniformly tapered post 8 that can be press-fit or friction-fit within a substantially uniformly tapered bore 6 to firmly mount the head component 4 to the stem 2.

The prosthesis 1 can be a modular prosthesis, meaning that a number of stem and head geometries can be provided from which a selection can be made that most closely approximates the natural joint components of the patient. Thus, the angle of the platform surface 5 can be different among stems 2. While all head components 4 will include a generally spherical bearing surface 9, the orientation of this surface relative to the platform surface 5 can be changed. Specifically, the location of the post 8 relative to the bearing surface 9 can be offset from the center of the surface (i.e., an eccentric head). In some cases, the angle of the post can be different between head components 4.

The exemplary joint prosthesis according to the present invention is modular and introduces an articulating mounting element 30, 130 between the stem 12 and a head component 20, as shown in FIGS. 2-4, 8 and 9. In one embodiment of the invention, the mounting element 30 includes a proximal portion 33 that mates with the head component 20. In a specific embodiment, the proximal portion 33 defines a tapered surface that is press-fit or friction-fit within a complementary bore 21 defined in the head component.

The first embodiment of the mounting element 30 further includes a frusto-spherical articulating portion 34. As at least partially discernable in the drawings, the actual surface of the articulating portion 34 includes only a partial sphere because the distal end of the articulating portion is a flat circular surface perpendicular to the axis of symmetry of the mounting element 30 and the proximal end of the articulating portion is integrally formed to the proximal portion 33. Hence, the articulating portion 34 is only partially spherical and, more specifically, is frusto-spherical. Nevertheless, it should be noted that the surface of the articulating portion 34 is contiguous and a substantial portion of the surface of the articulating portion 34, especially that portion which would be adjacent the equatorial region of a complete sphere having its poles intersected by the axis of symmetry of the mounting element 30 is substantially equidistant from a focus located on the axis of symmetry.

The articulating portion 34 is sized to achieve a press-fit engagement within the tapered bore 16 of the stem 12 when the portion 34 is pushed sufficiently far into the tapered bore 16. The partial spherical shape of the articulating portion 34 allows the mounting element 30 to rotate about three dimensional axes x, y, z when the articulating portion 34 contiguously engages the wall of the tapered bore 16 along a great circle of the partial spherical surface. Thus, the mounting element 30 can rotate about its own axis (the x axis), pivot about a version axis (they axis) or pivot about an inclination axis (the z axis). The mounting element 30 can rotate a full 360° about its own axis. However, the pivot range in the other two degrees of freedom is limited by contact between the articulating mounting element 30 or the head component and the platform surface 15 of the stem 12. The range of motion in these two degrees of freedom are maximized by the intermediate portion 35 connecting the articulating portion 34 to the proximal portion 33. In particular, the intermediate portion 35 can be angled away from the articulating portion 34 to form an inverted frusto-conical surface to provide clearance as the mounting element 30 is pivoted. While the illustrated proximal portion 33, articulating portion 34 and intermediate portion 35 are shown as being formed concentrically about the axis of symmetry of the mounting element 30, it is within the scope of the disclosure for the intermediate portion 35 and the proximal portion 33 to be formed about a second axis intersecting the axis of symmetry of the articulating portion 34 at an angle.

In one feature of the exemplary joint prosthesis, a second fixation capability is provided to augment the friction or press-fit between the articulating portion 34 and the tapered bore 16. In particular, a machine screw 40 is provided that includes a threaded portion 46 configured to mate with a threaded bore 18 in the stem 12. The bore 18 is concentrically disposed at the base of the tapered bore 16. The screw 40 is introduced into the threaded bore 18 through the articulating mounting element 30.

Figure 2:
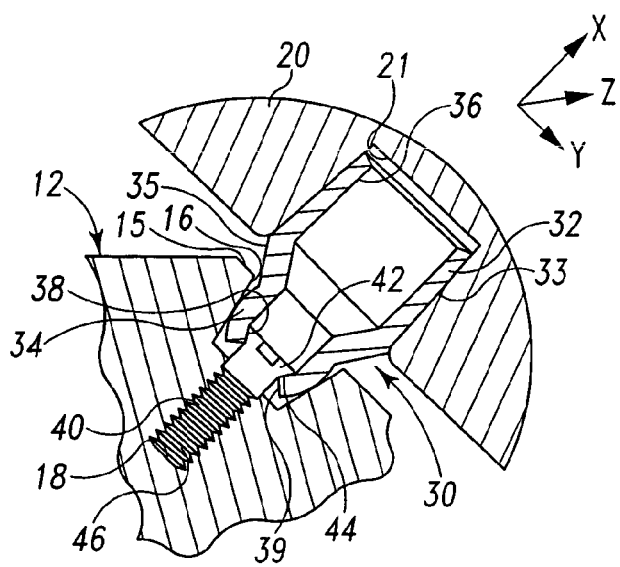
FIG. 2 is an enlarged cross-sectional view of a portion of an exemplary joint prosthesis according to the present invention.
Figure 3:
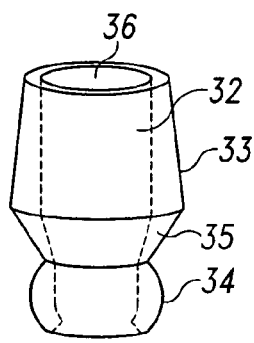
FIG. 3 is a front perspective view of an articulating mounting element used with the joint prosthesis of in FIG. 2.
Figure 4:
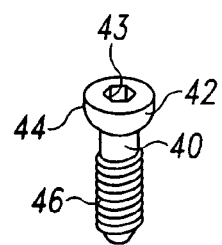
FIG. 4 is a front perspective view of a fixation screw used with the joint prosthesis of in FIG. 2.

As at least partially discernable in FIG. 2, the mounting element 30 defines a central passageway 36 that extends through the length of element 30 and that is open at its proximal and distal ends. The passageway defines an internal bearing surface 38 at the distal end of the element 30, or more specifically at the base of the articulating portion 34. The screw 40 includes a head 42 that includes an underside surface 44 that is complementary with the internal bearing surface 38. These two surfaces 38, 44 form a spherical bearing interface that allows the mounting element 30 to experience its full range of angular motion without interference from the screw 40, even when the screw 40 is loosely threaded into the threaded bore 18. The articulating portion 34 defines a relief 39 at the distal end of the passageway 36 to facilitate this full range of movement of the mounting element 30.

The passageway 36 in the mounting element 30 allows introduction of the screw 40 through the mounting element 30 and into the threaded bore 18. The screw 40 can be loosely threaded into the bore 18 to permit movement of the mounting element 30. Once the proper position for the mounting element 30 has been achieved, the screw 40 can be tightened using a tool engaged within the tool recess 43 on the head 42 of the screw 40. As the screw 40 is tightened, it drives the articulating portion 34 deeper into the tapered bore 16, thereby fixing the mounting element 30 against further articulation. The screw 40 thus combines with the friction or press-fit feature to lock the construct.

The articulating mounting element 30 can be utilized with the stem 12 engaged within the bone, such as the humerus. In order to determine the proper configuration for the joint prosthesis, a head component, such as component 20 is carried by the proximal portion 32 of the mounting element. As can be seen in FIG. 2, the head component 20 is closed over the passageway 36, thereby preventing access to the screw 40 unless the head portion is removed.

Figure 5:
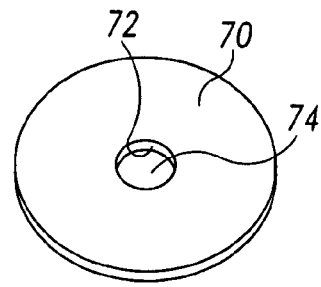
FIG. 5 is a bottom perspective view of a head component of the joint prosthesis of in FIG. 2.

In one embodiment, a head component 70 can be provided as at least partially discernable in FIG. 5 (which is a bottom perspective view of the head component 70). This head component 70 includes a tapered bore 72 that is configured for mating engagement with the proximal portion 32. However, unlike the head component 20, the bore 72 includes an opening 74 at the proximal face of the component. Thus, the opening 74 provides complete access to the screw 40, even when the head component 70 is mounted on the mounting element 30.

In use the mounting element 30 can be initially mated with a head component 70. The component can be a final component or a trial. In the preferred embodiment, the two components mate by way of a socket taper as is known in the art. The mounting element 30, with the head component 70 mounted thereon, can be maneuvered to position the articulating portion 34 within the tapered bore 16. The screw 40 can be introduced through the opening 74 and along the passageway 36 so that the screw can be threaded into the threaded bore 18 in the stem 12.

The screw 40 can be loosely tightened so that the articulating portion 34 can rotate, but the screw head 42 offers some resistance to help hold the head component 70 in position. The head component 70 can be manipulated as necessary to achieve an angular orientation that will mate efficiently with the opposite component of the joint (the glenoid component in the case of a shoulder prosthesis). The screw 40 can be tightened and loosened as necessary to hold the head component 70 in position to verify proper mating fit between the joint components.

If it is determined that a different head component is needed, the component can be removed from the mounting element 34 without disturbing the position of the mounting element relative to the stem 12. Once the proper head component 70 has been selected and situated at its optimum orientation, the screw 40 can be fully tightened into the bore 18.

Figure 6:
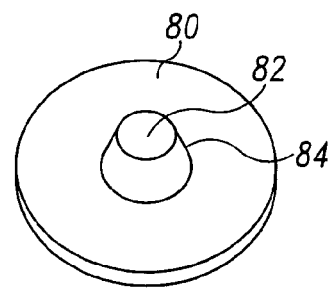
FIG. 6 is a bottom perspective view of an alternative head component for use with the joint prosthesis of FIG. 2.

Here, it is noted that the present invention provides, among other things, a modular system that can accommodate a wide range of joint constructs. For instance, a head component 80 can be provided as shown in FIG. 6. This head component includes a mounting post 82 with a tapered engagement surface 84 that is configured to be mounted directly within the tapered bore 16. The head component 80 can be used where no angular variations are required.

The head component 80 can also be press-fit into the passageway 36 of the mounting element 30. In this case, the passageway is formed as a tapered bore, similar to the tapered bore 16 in the stem 12. With this specific embodiment, the post 82 can define a bore therethrough that communicates with the passageway 36 in the mounting element to permit introduction of the screw 40 therethrough.

Figure 7:
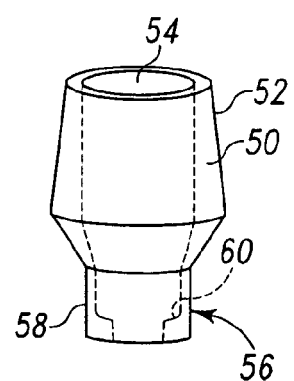
FIG. 7 is a front perspective view of an alternative mounting element that can substitute for the articulating mounting element in the joint prosthesis of FIG. 2.

A further component of the modular system is the fixed mounting element 50 shown in FIG. 7. This fixed element includes a mounting portion 56 having a tapered surface 58 configured for press or friction-fit engagement with the tapered bore 16. The proximal portion 50 can have a tapered surface 52 for engagement within the bore 21 of the head component 20 (FIG. 2), or within the bore 72 of the head component 70 (FIG. 5). As is apparent from FIG. 7, the mounting element 50 does not accommodate changes in version or inclination angle, the degrees of freedom of movement of the element being limited to the longitudinal axis of the element.

The mounting element 50 can include a bore 54 that can be tapered to receive the post 82 of the head portion 80 (FIG. 6). In addition, the bore can provide a passageway for introduction of a mounting screw, like the screw 40 depicted in FIG. 4. The bore can form a bearing surface 60 against which the surface 44 of the screw 40 bears to clamp the mounting element 50 to the stem 12.

The exemplary embodiment includes a machine screw 40 for final securing of the mounting element 30 to the stem by way of the mating threaded bore 18. Other forms of mechanical fastener are contemplated that can effect final fixation of the mounting element to the stem. For instance, a press-fit pin can be provided that is pressed into a complementary bore (in lieu of the threaded bore 18). The pin would retain the configuration of the head 42 of the screw 40, most particularly the spherical underside surface 44 and would operate to press the articulating portion 34 into the tapered bore 16.

Figure 8:
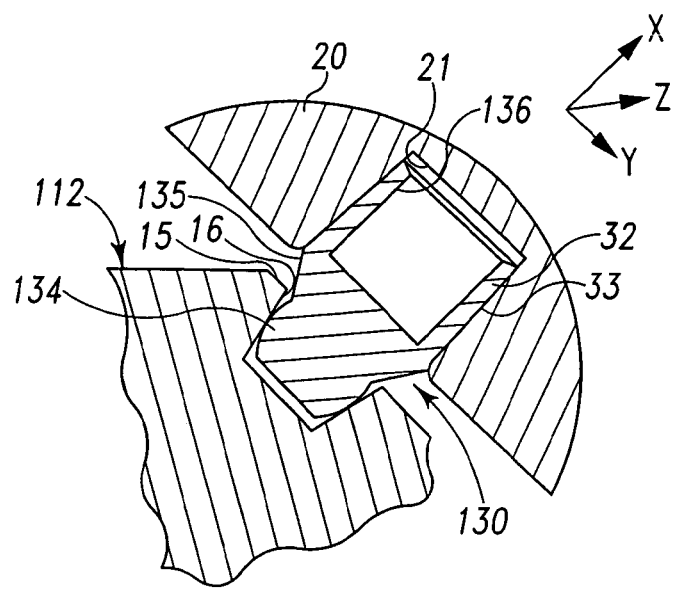
FIG. 8 is an enlarged cross-sectional view of a portion of an exemplary alternative joint prosthesis according to the present invention.
Figure 9:
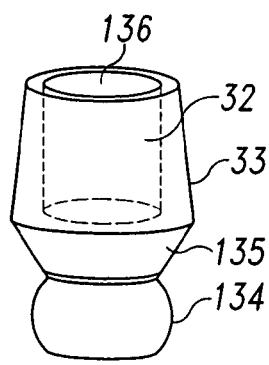
FIG. 9 is a front perspective view of an alternative mounting element particularly configured to be used with the joint prosthesis of FIG. 8 and capable of being utilized with the joint prosthesis of in FIG. 2.

As shown, for example, in FIGS. 8 and 9, an exemplary alternative joint prosthesis according to the present invention includes a head component 20, an alternative embodiment of the stem 112, and an alternative embodiment of the mounting element 130. The alternative embodiment of the stem 112 is substantially identical to the prior art stem 12 except that the alternative embodiment of the stem 112 is not formed to include the threaded bore 18. Illustratively, the head component 20 is identical to head component 20 of the exemplary joint prosthesis of FIG. 2.

The mounting element 130 is also substantially similar to mounting element 30 so similar reference numerals will be used to describe similar components and identical reference numerals will be utilized to describe identical components. The mounting element 130 is formed to include a bore 136 extending through an opening in the proximal end of the proximal portion 33 and only partially through the mounting element 130 instead of the passageway 36 formed in mounting element 30. Thus, mounting element 130 is configured for utilization without the screw 40 for locking the orientation of the mounting element 130 relative to the stem 112.

The mounting element 130 includes a proximal portion 33 that mates with the head component 20. In a specific embodiment, the proximal portion 33 defines a tapered external surface that is press-fit or friction-fit within a complementary bore 21 defined in the head component.

As at least partially discernable in FIGS. 8 and 9, the mounting element 130 further includes a solid frusto-spherical articulating portion 134. As at least partially discernable in the drawings, the actual surface of the articulating portion 134 includes only a partial sphere because the distal end of the articulating portion is a flat circular surface perpendicular to the axis of symmetry of the mounting element 130 and the proximal end of the articulating portion is integrally formed to the proximal portion 33. Hence, the articulating portion 134 is only partially spherical and, more specifically, is solid and frusto-spherical. Nevertheless, it should be noted that the surface of the articulating portion 134 is contiguous and a substantial portion of the surface of the articulating portion 134, especially that portion which would be adjacent the equatorial region of a complete sphere having its poles intersected by the axis of symmetry of the mounting element 130 is substantially equidistant from a focus located on the axis of symmetry.

The articulating portion 134 is sized to achieve a press-fit engagement within the tapered bore 16 of the stem 12 when the portion 134 is pushed sufficiently far into the bore. When pushed into the tapered bore 16 by hand or otherwise, the frictional forces created by the press-fit engagement are sufficient to maintain the orientation of the mounting element 130 relative to the stem 112 even when the head component is coupled to the mounting element 130 so long as the component is not subjected to a load. Once it is established that the component has the desired orientation, the articulating portion 134 is pressed or driven further into the tapered bore 16 by impaction, by hand, or otherwise to mechanically lock the mounting element 130 in the desired orientation relative to the stem 112. Alternatively, the mounting element 130 is chilled to reduce the diameter of the articulating portion 134 or the stem is warmed to increase the diameter of the tapered bore 16 to facilitate seating and locking the mounting element relative to the stem 112. Thus, the mounting element 130 avoids use of the locking screw 40. Once the mounting element 130 is locked in the desired location, the component can be subjected to the loads and stresses normally associated with the joint that it is partially replacing without the mounting element changing its orientation.

The frusto-spherical shape of the articulating portion 134 allows the mounting element 130 to rotate about three dimensional axes x, y, z. Thus, the mounting element 130 can rotate about its own axis (the x axis), pivot about a version axis (the y axis) or pivot about an inclination axis (the z axis). The mounting element 130 can rotate a full 360° about its own axis. However, the pivot range in the other two degrees of freedom is limited by contact between the articulating mounting element or the head component and the platform surface 15 of the stem 112. The range of motion in these two degrees of freedom are maximized by the intermediate portion 135 connecting the articulating portion 134 to the proximal portion. In particular, the intermediate portion 135 can be angled away from the articulating portion 134 to provide clearance as the mounting element 130 is pivoted.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, while the illustrated embodiments relate to a humeral component of a shoulder prosthesis, the connection element of the present invention can be utilized in other joints such as hip, knee, or elbow joints to engage a joint component to a bone engaging component of the prosthesis.

Furthermore, while the preferred embodiment contemplates angular adjustment capabilities in all degrees of freedom, the mounting element can be configured to limit angular movement to specific directions. For instance, instead of a spherical interface, the articulating portion 34, 134 can include a flat side opposing a corresponding flat side to the tapered bore 16 such that rotation of the portion 34, 134 between the two flat sides is prohibited.

What is claimed is:

1. A method for mounting a joint component to a bone, the method comprising:

inserting a stem into the bone;

positioning a solid articulating portion of a mounting element within a tapered bore associated with the stem so that the mounting element is substantially free to pivot in multiple degrees of freedom relative to the stem while maintaining substantially contiguous engagement between the solid articulating portion and a portion of a surface of the tapered bore defining a circle; wherein positioning the solid articulating portion of the mounting element within the tapered bore comprises: positioning an inverted frusto-spherical portion of the mounting element adjacent to a proximal end of the tapered bore;

engaging the joint component to a proximal portion of the mounting element;

manipulating the mounting element to vary an angular position of the joint component relative to the stem with the mounting element positioned in the tapered bore while maintaining substantially contiguous engagement between the solid articulating portion and the portion of the surface of the tapered bore defining the circle; and mechanically locking the solid articulating portion in the tapered bore to fix a position of the mounting element relative to the stem after manipulating the mounting element by forcing the solid articulating portion toward a bottom of the tapered bore without the use of a separate mechanical fastener.

2. The method of claim 1, wherein:

the tapered bore extends from a proximal surface of the stem; and positioning the solid articulating portion of the mounting element within the tapered bore comprises positioning the inverted frusto-spherical portion of the mounting element adjacent to the proximal end of the stem.

3. The method of claim 1, wherein mechanically locking the solid articulating portion in the tapered bore comprises:

chilling the solid articulating portion; and inserting the chilled solid articulating portion into the tapered bore.

4. The method of claim 1, wherein mechanically locking the solid articulating portion in the tapered bore comprises:

heating the tapered bore; and inserting the solid articulating portion into the heated tapered bore.

5. The method of claim 1, wherein positioning the solid articulating portion of the mounting element within the tapered bore includes press-fitting the solid articulating portion into the tapered bore.

6. The method of claim 5, wherein the press-fitting is limited to press-fitting the solid articulating portion into the tapered bore by hand.

7. The method of claim 5, wherein mechanically locking the solid articulating portion in the tapered bore comprises driving the solid articulating portion toward the bottom of the tapered bore.

8. A method for mounting a joint component to a bone, the method comprising:

inserting a stem into the bone;

positioning a solid articulating portion of a mounting element within a tapered bore associated with the stem so that the mounting element is substantially free to pivot in multiple degrees of freedom relative to the stem while maintaining substantially contiguous engagement between the solid articulating portion and a portion of a surface of the tapered bore defining a circle; wherein positioning the solid articulating portion of the mounting element within the tapered bore comprises: positioning an inverted frusto-spherical portion of the mounting element adjacent to a proximal end of the tapered bore;

engaging the joint component to a proximal portion of the mounting element;

manipulating the mounting element to vary an angular position of the joint component relative to the stem with the mounting element positioned in the tapered bore while maintaining substantially contiguous engagement between the solid articulating portion and the portion of the surface of the tapered bore defining the circle; and mechanically locking the solid articulating portion in the tapered bore to fix a position of the mounting element relative to the stem after manipulating the mounting element by forcing the solid articulating portion toward a bottom of the tapered bore by heating the tapered bore and inserting the solid articulating portion into the heated tapered bore.

9. The method of claim 8, wherein:

the tapered bore extends from a proximal surface of the stem; and positioning the solid articulating portion of the mounting element within the tapered bore comprises positioning the inverted frusto-spherical portion of the mounting element adjacent to the proximal end of the stem.

10. The method of claim 8, wherein mechanically locking the solid articulating portion in the tapered bore comprises:

chilling the solid articulating portion; and inserting the chilled solid articulating portion into the heated tapered bore.

11. The method of claim 8, wherein positioning the solid articulating portion of the mounting element within the tapered bore includes press-fitting the solid articulating portion into the tapered bore.

12. The method of claim 11, wherein the press-fitting is limited to press-fitting the solid articulating portion into the tapered bore by hand.

13. The method of claim 11, wherein mechanically locking the solid articulating portion in the tapered bore comprises driving the solid articulating portion toward the bottom of the tapered bore.

* * * * *